United States Patent [19]
Berger et al.

[11] Patent Number: 5,611,506
[45] Date of Patent: Mar. 18, 1997

[54] DIALYSIS ASSIST DEVICE

[76] Inventors: Maria Berger; Nancy Page; Sharon L. Mroz, all of 710 Park Pl., Mishawaka, Ind. 46545

[21] Appl. No.: 507,658

[22] Filed: Jul. 25, 1995

[51] Int. Cl.$^6$ .................................................. F16L 3/08
[52] U.S. Cl. ............................................................ 248/65
[58] Field of Search .................................. 248/65, 73, 75, 248/81, 49, 56, 222.12, 223.41

[56]     References Cited

U.S. PATENT DOCUMENTS

| 5,098,048 | 3/1992 | Chen | 248/65 X |
| 5,100,393 | 3/1992 | Johnson | 248/74.3 X |
| 5,323,992 | 6/1994 | Sifers et al. | 248/65 X |

*Primary Examiner*—Ramon O. Ramirez
*Attorney, Agent, or Firm*—Baker & Daniels

[57]  ABSTRACT

A dialysis assist device for use by peritoneal dialysis patients facilitates connection of tubing communicating fluid bags with a catheter implanted in the dialysis patient. The assist device includes a tray which includes a groove extending through the tray which receives tubing and a connecter for connecting the tubing to the catheter. The connecter includes a flange that is received in a groove in the aperture, thereby holding the connecter while the patient connects the catheter to the connecter. Receptacles are provided for receiving the used cap covering the catheter and for assisting the patient in connecting a new sterile cap to the catheter when dialysis has been completed.

12 Claims, 10 Drawing Sheets

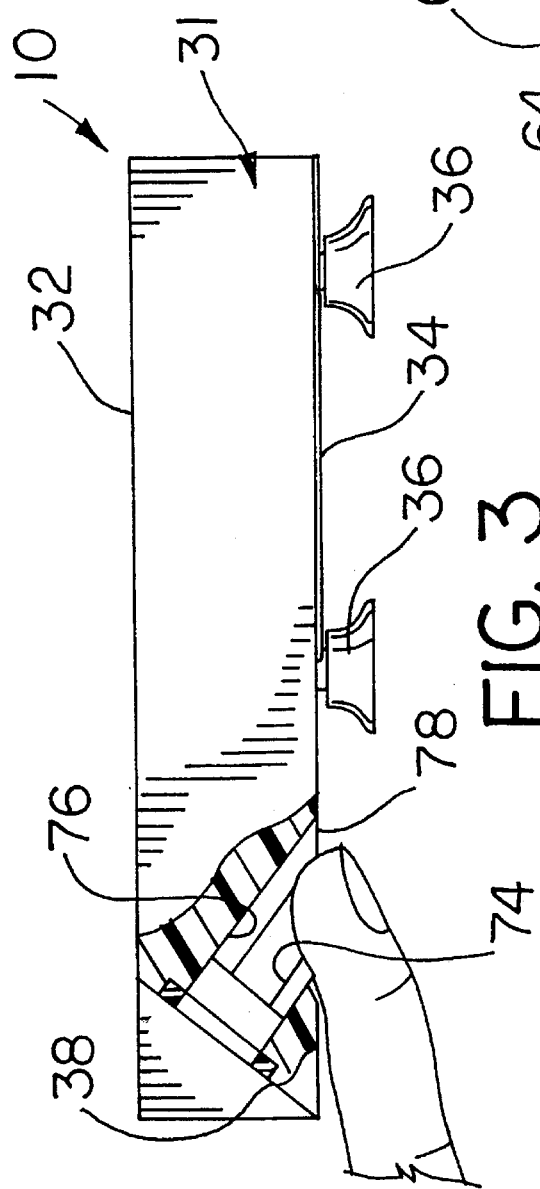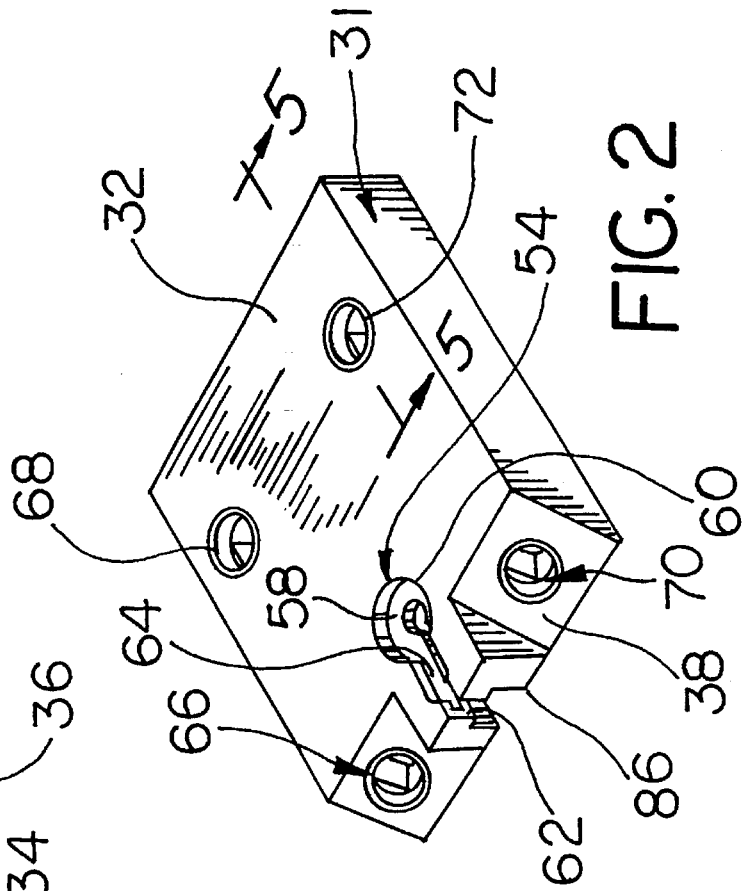

5,611,506

DIALYSIS ASSIST DEVICE

This invention relates to a dialysis assist device to facilitate the exchange of fluids for peritoneal dialysis patients.

Peritoneal dialysis patients must exchange peritoneal fluids many times a day. Exchange of fluids is effected through a catheter that is surgically implanted into the abdomen of the patient. When the patient is to begin a dialysis procedure, the catheter must be connected to tubing which is connected both to an empty bag and to a bag containing dialysis fluid. After draining fluid into the empty bag, the patient connects the catheter to the tube connected to the bag containing the dialysis fluid, to thereby replenish the peritoneal fluid. Obviously, great care must be taken to assure that the catheter and the dialysis equipment remains sterile. Furthermore, dialysis patients commonly have multiple physical dysfunctions, and many are elderly. Accordingly, it is difficult for many dialysis patients to routinely make the required connections between the catheter and the dialysis equipment while maintaining the necessary sterile environment.

The present invention provides a tray that can be mounted on any level surface and provides a convenient support for the connecting device that connects the catheter to the fresh fluid supply. The device is designed so that all the required connections can be made by using only one hand. Receptacles are provided for receiving the used cap which closes off the catheter, and for holding a new sterile cap for installation on the catheter after dialysis has been complex:ed. As discussed above, many dialysis patients have multiple physical dysfunctions, and commonly have good use of only one hand. Accordingly, the present invention enables patients who have use of only one hand routinely perform the required dialysis without assistance.

These and other advantages of the present invention will become apparent from the following description with reference to the accompanying drawings, in which:

FIG. 2 is a view in perspective of a dialysis assist device made pursuant to the teachings of the present invention;

FIG. 3 is a side elevational view, partly in section, of the dialysis assist device illustrated in FIG. 2, and further illustrating the manner in which used caps are removed from the device and disposed of;

Figure 12:
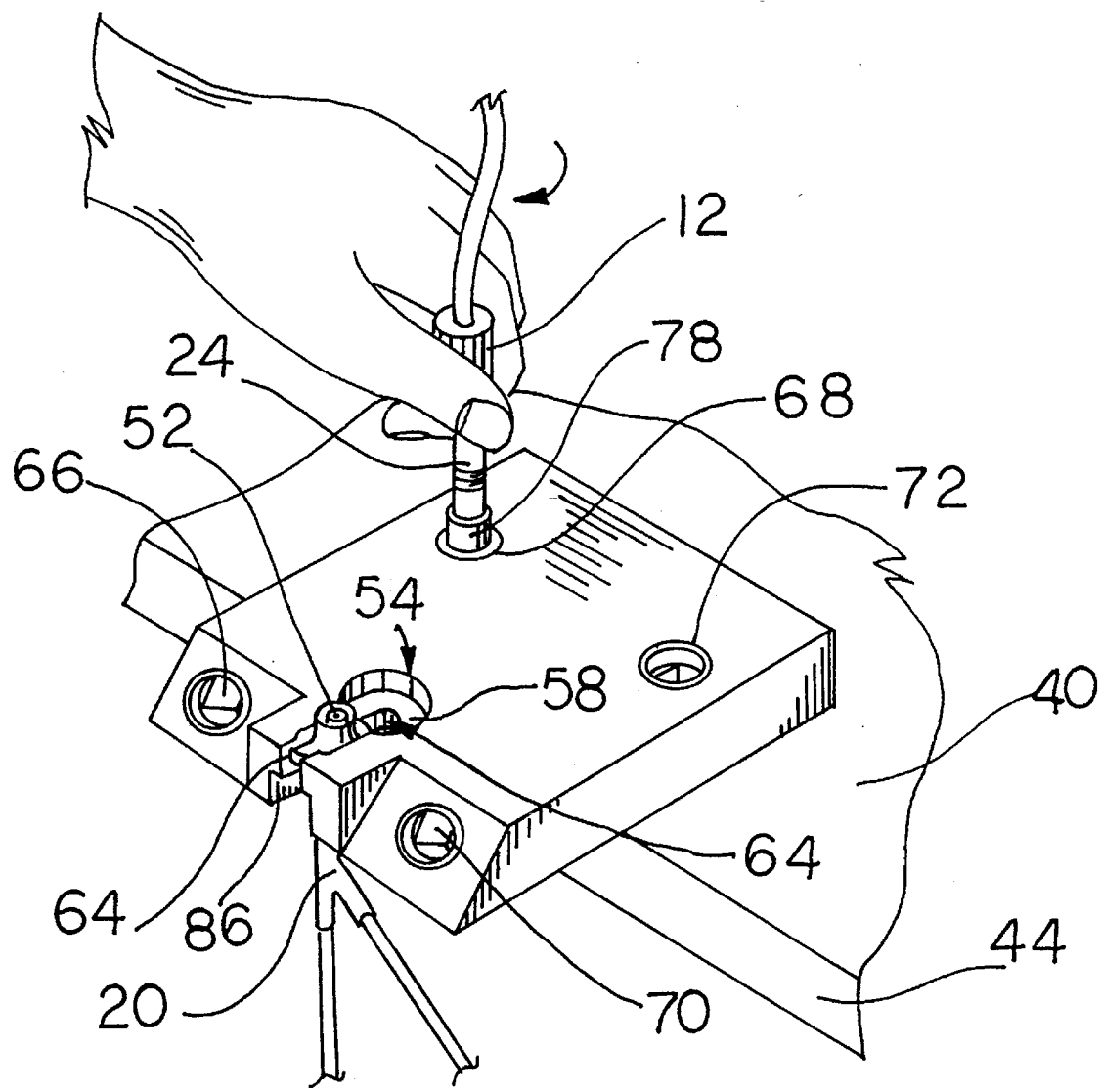

FIGS. 6–11 are views of the dialysis assist device according to the present invention illustrating step-by-step the manner in which the connective tubing is installed on the assist device and the manner in which the catheter is connected to the tubing; and FIG. 12 is a view of the assist device according to the present invention illustrating the manner in which a new sterile cap is installed on the catheter after dialysis has been completed.

Referring now to the drawings, a dialysis assist device generally indicated by the numeral 10 is used to support a connecter 12 which is connected by tubing 14 to an empty bag 16 for receiving fluid through a "Y" connection 20. Tubing 18 is connected to "Y" connection 20 and to another bag 22 which stores dialysis fluid. Connecting device 12 connects with a screw connecter 24 which is part of a catheter 16 which is surgically implanted as at 28 in the abdomen of a patient 30. Tubing 18 is initially clamped off during dialysis to first permit peritoneal dialysis fluid to be drained from the patient into the empty bag 16, whereupon the tubing 14 is clamped off and the tubing 18 is opened to permit infusion of dialysis fluid for the bag 22 into the abdomen of the patient. Commonly, the exchange of fluids must be effected several times a day. The dialysis assist device 10 permits a patient who may have multiple other dysfunctions to effect dialysis without assistance, even if the patient only has use of one hand.

The dialysis assist device 10 includes a tray 30 having an upper surface 32 and a lower surface 34. Conventional suction cups 36 are mounted on the lower surface 34 and are offset from the forward face 38 of the tray 30 to permit mounting of the tray 30 on a horizontal support surface, such as a table 40 with a forward portion 42 of tray 30 suspended over the edge 44 of the table 40.

The connecter 12 extends from the "Y" connection 20 and includes a circumferentially-extending, radially-outwardly projecting flange 46 and a plug 48 which can be removed by grasping ring 50 to expose a receptacle 52 for connection with the screw connecter 24 of catheter 26. The tray 31 includes a keyhole-shaped aperture 54 that extends through the tray between the upper surface 32 and the lower surface 34. The aperture 54 is defined by a stepped wall 56 defining a support surface 58. Aperture 54 further includes a larger diameter portion 60 which extends into a narrower, elongated portion 62. A groove 64 is defined in opposite sides of that portion of the wall defining the narrower portion 62 of aperture 54. The groove 64 extends substantially parallel to the surfaces 32 and 34.

The tray 31 is further provided with a first pair of recesses 66, 68 and a second pair of recesses 70, 72 which are used by the dialysis patient to facilitate removal of the cap covering the end of the connecter 24 when the catheter 26 is not being used, and for installation of a new sterile cap after the exchange of fluids is completed. The apertures 66 and 68 are used by left-handed patients and the apertures 70 and 72 are used by right-handed patients so that the hand of the patient does not have to cross the sterile plane around the aperture 54. As seen in FIG. 3, each of the apertures 66 and 70 include diametrically-opposed flats 74 and 76, which engage corresponding flats (not shown) on the cap 78 to prevent the cap 78 from turning as the connecter 24 is unscrewed from the cap. Accordingly, when the patient 30 wishes to begin dialysis, he positions his catheter (in the case of a left-hand person) so that the cap at the end of the catheter is positioned in opening 66, and then unscrews the catheter. The cap can be removed from the aperture 66 or 70 by the patient placing the tip of his finger in an opening 78 in the lower surface 34 of tray 31, as illustrated in FIG. 3. Similarly, the openings 68 and 72 are provided with opposed flats 80, 82. When the exchange of fluids is completed, the patient removes a new sterile cap from a sealed packet and places it in one of the apertures 68, 72, with the flats (not shown) on the cap engaging the flats 80 and 82 of the aperture 68 or 72. The catheter connecter 24 can then be screwed into the cap, and the cap pulled out of the aperture with the catheter 76 before the latter is tucked away inside the patient's clothing. Washers 84 of a color contrasting to that of the material in which the tray is made are providing outlining the apertures 66, 68 and 70 and 72 to make them more easily identifiable to the patient.

Figure 1:
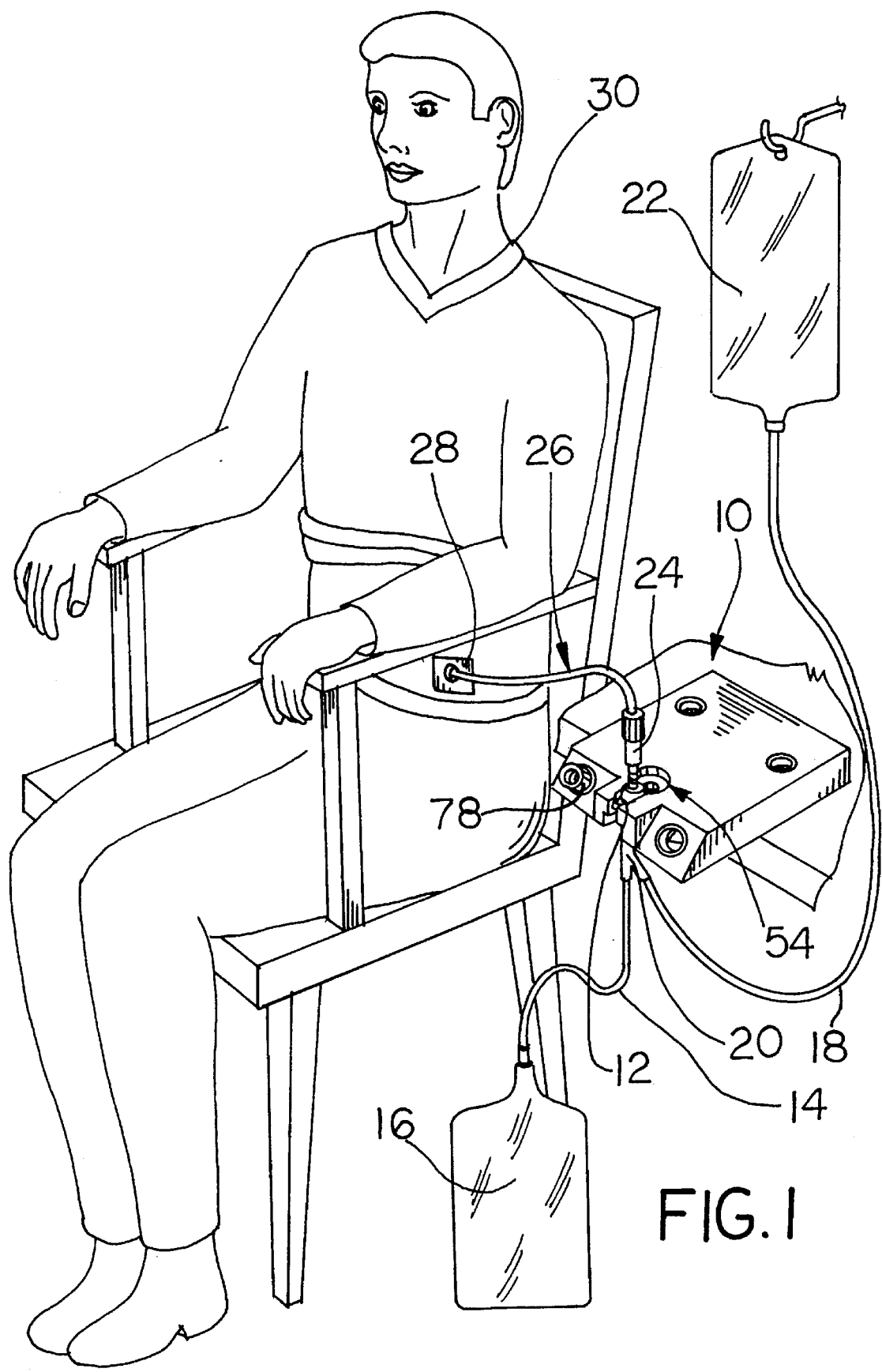
FIG. 1 is a view in perspective of a dialysis patient using the dialysis assist device of the present invention.
Figure 4:
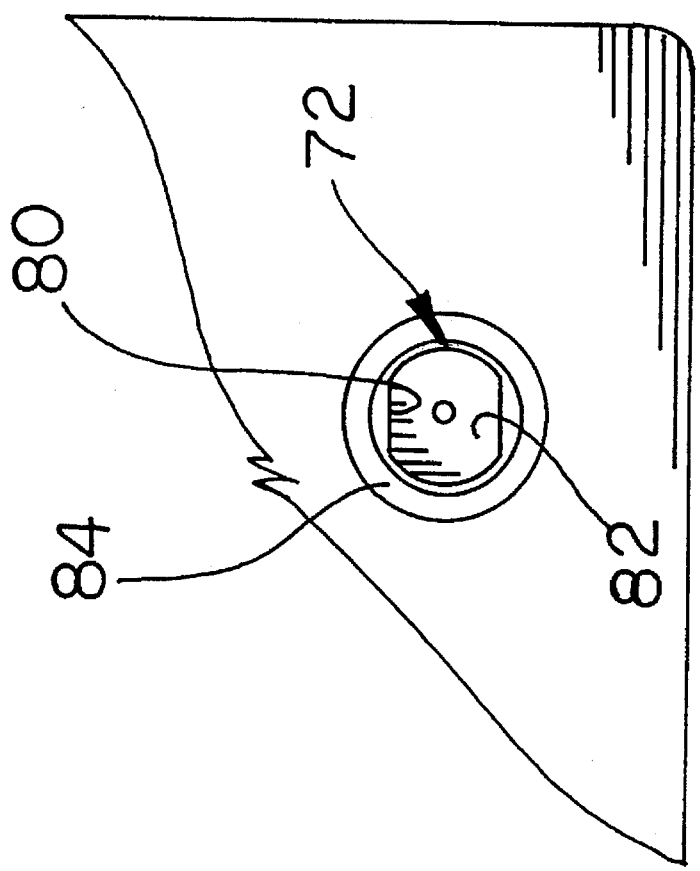
FIG. 4 is an enlarged, fragmentary view of one of the cap receptacle in the upper surface of the dialysis assist device.
Figure 5:
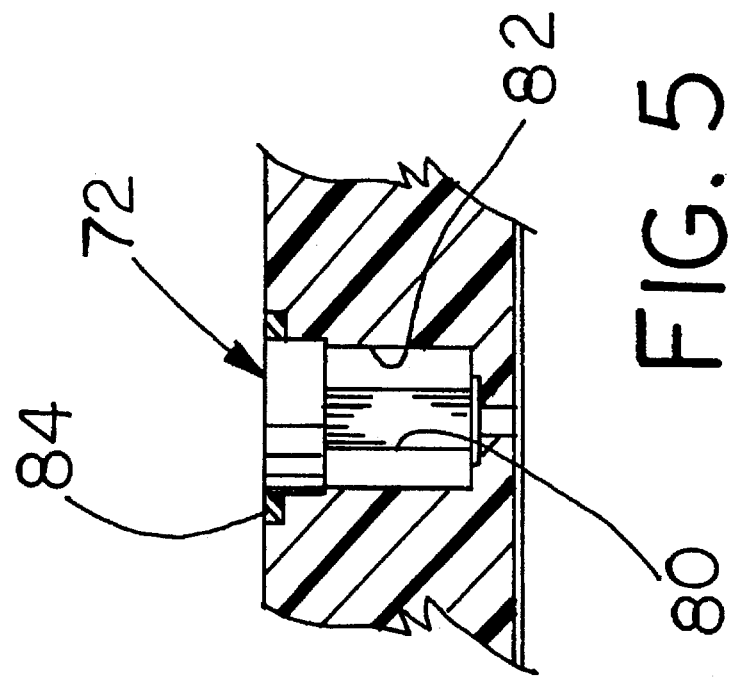
FIG. 5 is a view taken substantially along lines 5—5 of FIG. 2.
Figure 6:
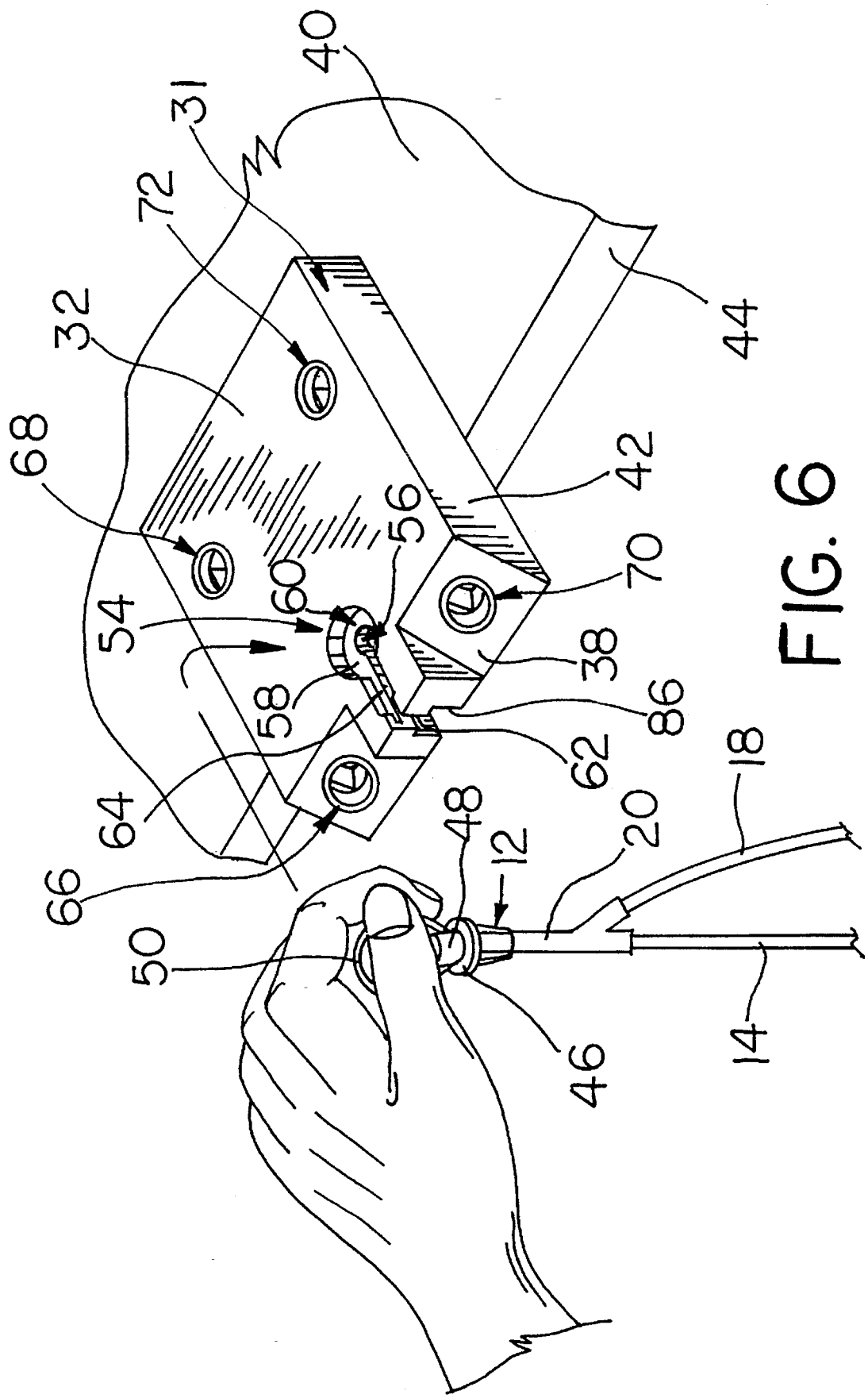
Figure 7:
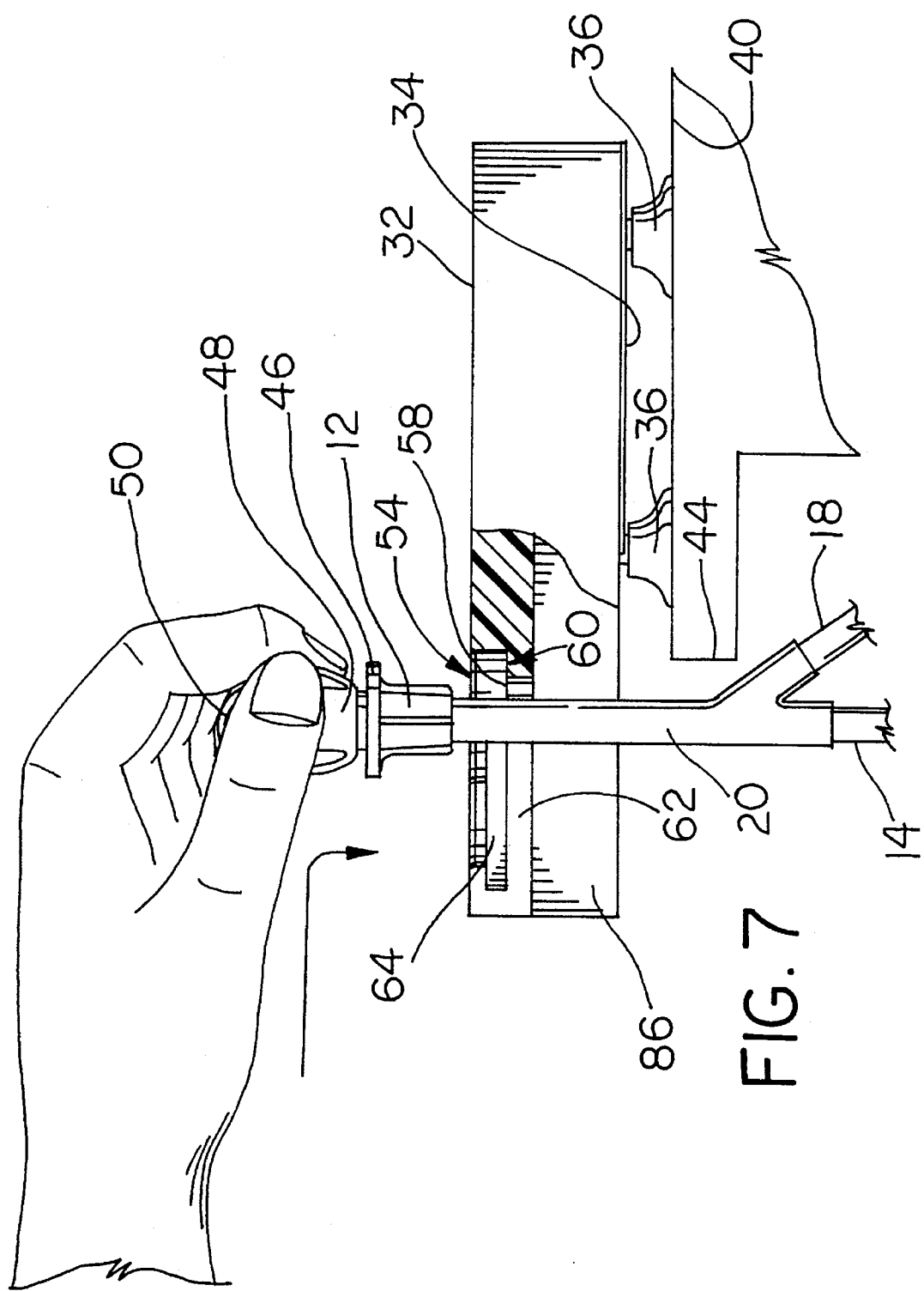
Figure 8:
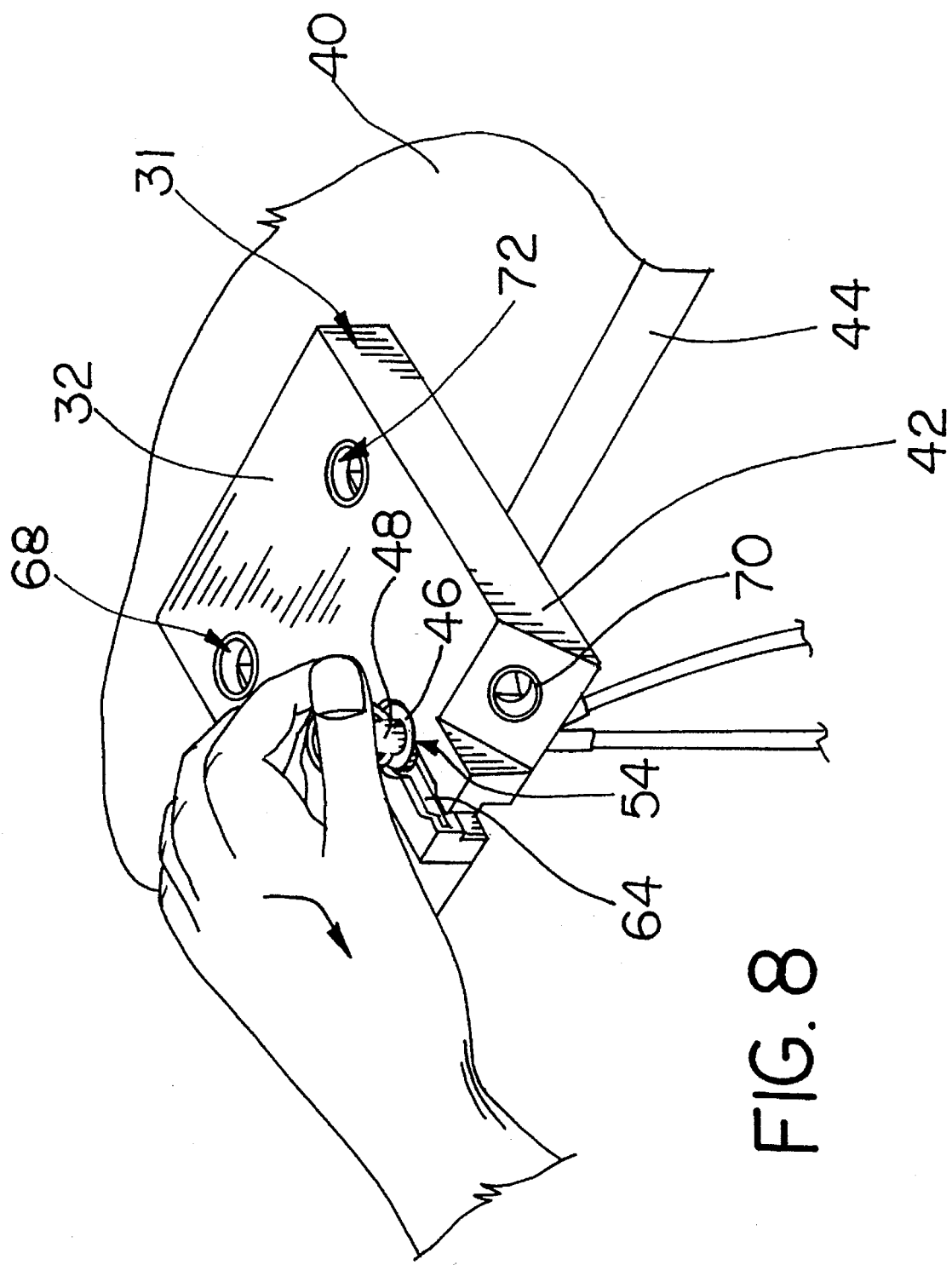
Figure 9:
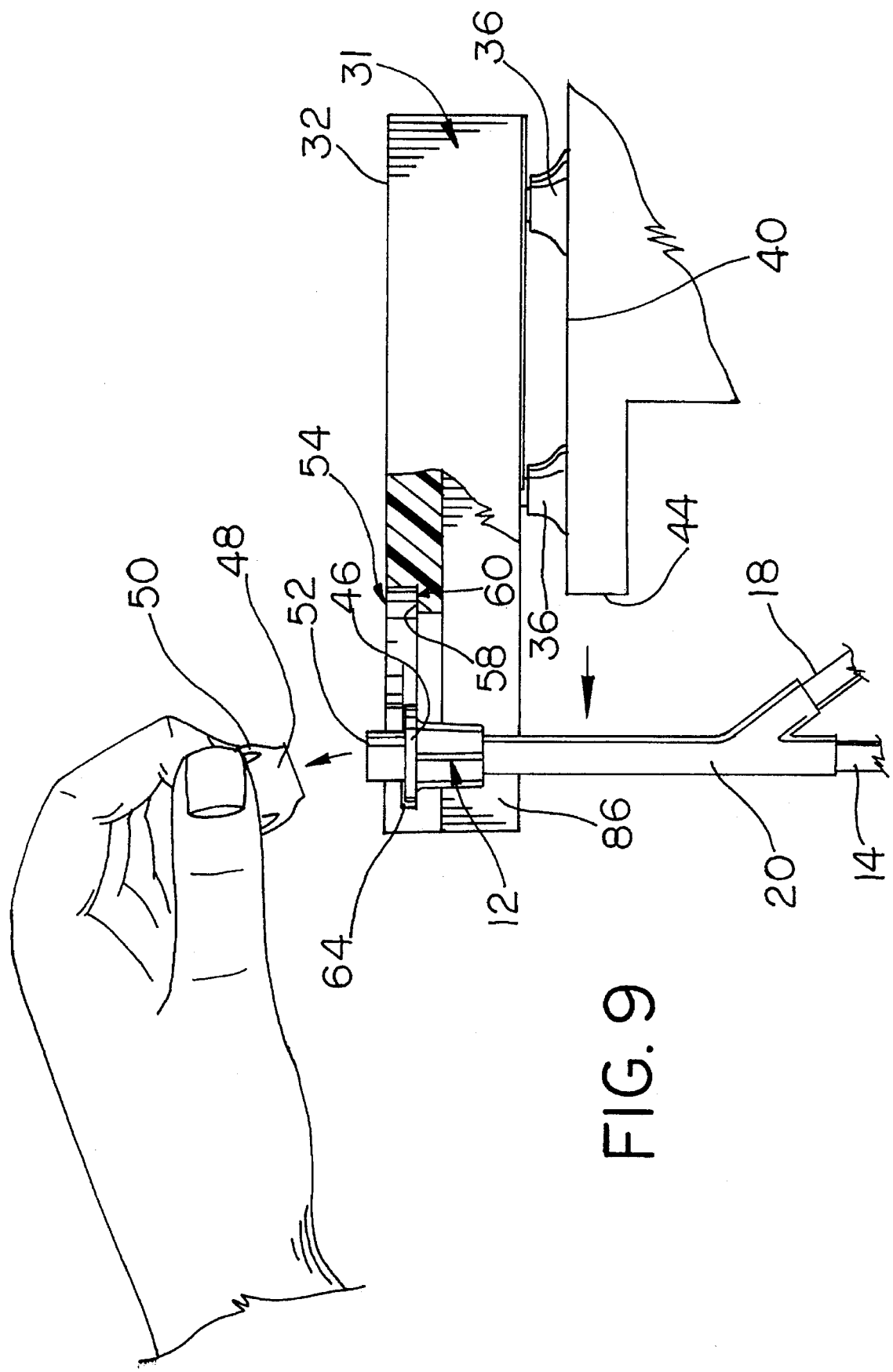
Figure 10:
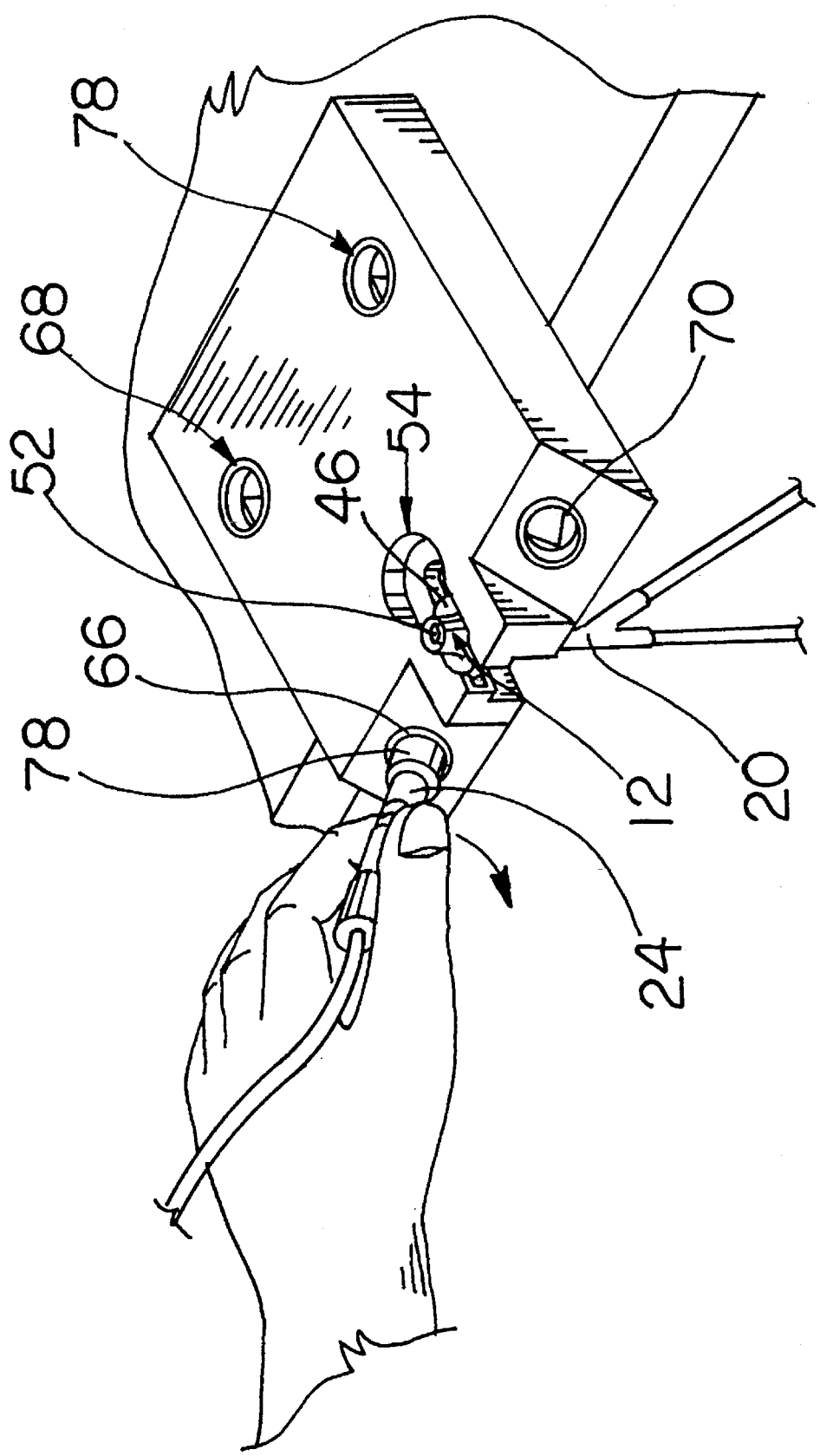
Figure 11:
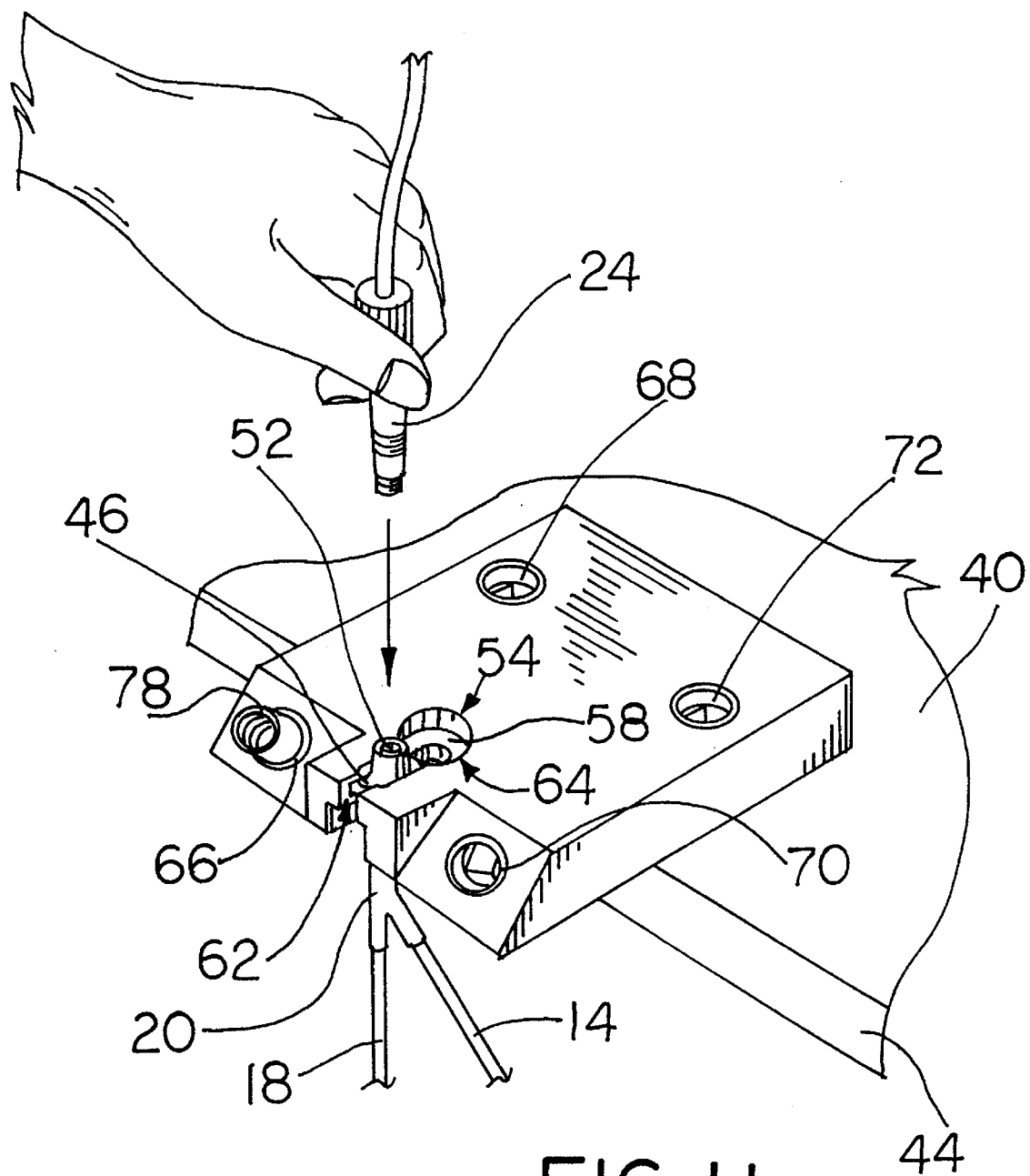

The patient prepares for dialysis by arranging the dialysis apparatus including the bags 16 and 22, the tubes 14,18 and the connecter 12 as illustrated in FIG. 1. This is accomplished by holding the plug 48 by the ring 50, and then bringing the connecter 20 through the open end of the aperture 54, through the smaller portion 62 of the aperture and into the larger portion 60. The flange 46 is then forced downwardly, as illustrated in FIG. 7, such that the flange rests on the support surface 58. The connecter 12 then is moved into the smaller portion 62 of the groover aperture 54 so that the flange 46 enters the groove 64 on opposite sides of the smaller portion 62. Accordingly, the connecter is held in the groove 64 in a stable position so that the patient is not required to hold both the catheter and the connecter to connect the catheter to the dialysis equipment. When the flange 48 is properly positioned in the groove 64, the Y-shaped connecter 20 extends through the bottom of the groove 86, as illustrated in FIG. 1. As illustrated at 59, the plug 48 can then be pulled off of the connecter 12. It will be noted that installation of the connecter 12 in the groover aperture 54 and engagement of the flange 46 into the groove 64 and removal of the plug 48 can all be effected in one motion using only a single hand. Accordingly, dialysis patients with use of only one hand can effect dialysis without assistance using the tray 31.

After the connecter 12 with flange 46 is properly positioned in the groove 64 and the plug 48 is removed, the cap 78 is removed from the end of the connecter 24 of catheter 26 as described above. Catheter 26 is then screwed into connecter 12 to permit communication of dialysis fluids through the receptacle 52 and into the catheter 26. After dialysis has been completed, the connecter 24 of catheter 26 is unscrewed from the connecter 12 and a new cap is installed on the connecter 24 as described above by using one of the opening of aperture 68 or 72. The dialysis is now complete, and the bags 16, 22 with tubing 14 and 18 and connecter 12 can now be disposed of.

What is claimed is:

1. Dialysis assist device to facilitate connection of tubing with a catheter implanted in a dialysis patient for transferring dialysis fluid to and from said catheter, the catheter and the tubing having cooperating releasable connecting means, said dialysis assist device comprising a tray, securing means for releasably securing said tray against movement relative to a support surface, said tray including an aperture extending through said tray for receiving said tubing during dialysis, and attaching means for attaching the connecting means of the tubing to said tray for connection with the connecting means of the catheter.

2. Dialysis assist device as claimed in claim 1, wherein said aperture is defined by a wall, said wall having a groove for receiving a flange carried by said tubing for securing the tubing within said groove and orienting said connecting means for said tubing for connection with the connecting means of the catheter.

3. Dialysis assist device to facilitate connection of tubing with a catheter implanted in a dialysis patient for transferring dialysis fluid to and from said catheter, the catheter and the tubing having cooperating releasable connecting means, said dialysis assist device comprising a tray, securing means for releasably securing said tray on a support surface, said tray including an aperture extending through said tray for receiving said tubing during dialysis, and attaching means for attaching the connecting means of the tubing to said tray for connection with the connecting means of the catheter, said aperture being defined by a wall, said wall having a groove receiving a flange carried by said tubing for securing the tubing within said groove and orienting said connecting means of said tubing for connection with the connecting means of the catheter, said tray having a pair of opposite surfaces, said aperture and said wall extending between said surfaces, said groove being formed in said wall and extending substantially parallel to said surfaces.

4. Dialysis assist device as claimed in claim 3, wherein said wall includes a pair of opposed, parallel portions, said groove having parallel sections in each of said parallel portions receiving corresponding portions of said flange.

5. Dialysis assist device as claimed in claim 4, wherein said securing means are mounted on one of said surfaces, said securing means being offset from said aperture whereby said tray can be mounted adjacent an edge of said support surface with the aperture extending over said edge of the support surface, whereby said tubing can extend through said aperture and along said edge of the support surface.

6. Dialysis assist device as claimed in claim 3, wherein said aperture includes a narrower portion extending between said surfaces and a wider portion cooperating with the narrower portion to define a support surface therebetween, said tubing extending through said narrower portion, said flange being support upon said support surface.

7. Dialysis assist device as claimed in claim 6, wherein said groove is defined between said support surface and an inwardly projecting portion of said tray overlying a portion of said support surface, said support surface including another portion receiving said flange to permit the flange to be installed in said another portion and then moved into said groove to thereby retain the flange on the tray.

8. Dialysis assist device as claimed in claim 3, wherein said tray includes a pair of recesses for holding a cap closing said catheter when the catheter is not in use, one of said recesses holding a cap removed from said catheter before connection of the connection means of the catheter with the connecting means of the tubing, the other recess holding the cap to be placed on the catheter after the connection means of the catheter is disconnected from the connection means of the tubing.

9. Dialysis assist device as claimed in claim 8, wherein said aperture has an axis of symmetry, there are two pairs of said recesses for holding said caps, one pair of said recess being on one side of said axis of symmetry, the other pair being on the other side of said axis of symmetry.

10. Dialysis assist device as claimed in claim 8, wherein an opening in one of said surfaces intersects with said one recess to facilitate removal of the cap from the recess.

11. Dialysis assist device as claimed in claim 8, wherein each of said recesses include flats engaging corresponding flats on the caps to prevent rotation of the latter relative to the tray.

12. Dialysis assist device to facilitate connection of tubing with a catheter implanted in a dialysis patient for transferring dialysis fluid to and from said catheter, the catheter and the tubing having cooperating releasable connecting means, said dialysis assist device comprising a tray, securing means for releasably securing said tray on a support surface, said tray including an aperture extending through said tray for receiving said tubing during dialysis, and attaching means for attaching the connecting means of the tubing to said tray for connection with the connecting means of the catheter, said aperture being defined by a wall, said wall having a groove receiving a flange carried by said tubing for securing the tubing within said groove and orienting said connecting means of said tubing for connection with the connecting means of the catheter, said tray including a pair of recesses for holding a cap closing said catheter when the catheter is not in use, one of said recesses holding a cap removed from said catheter before connection of the connection means of the catheter with the connecting means of the tubing, the other recess holding the cap to be placed on the catheter after the connection means of the catheter is disconnected from the connection means of the tubing.

* * * * *